(12) United States Patent
Fulton et al.

(10) Patent No.: US 8,911,682 B2
(45) Date of Patent: Dec. 16, 2014

(54) METHOD FOR PRODUCING TISSUE MICROARRAY BLOCKS

(75) Inventors: Regan Spencer Fulton, Sausalito, CA (US); William Scott Crawford, Palo Alto, CA (US)

(73) Assignee: Array Science, LLC, Sausalito, CA (US)

( * ) Notice: Subject to any disclaimer, the term of this patent is extended or adjusted under 35 U.S.C. 154(b) by 705 days.

(21) Appl. No.: 12/156,700

(22) Filed: Jun. 4, 2008

(65) Prior Publication Data

US 2008/0318805 A1 Dec. 25, 2008

Related U.S. Application Data

(60) Provisional application No. 60/933,968, filed on Jun. 8, 2007.

(51) Int. Cl.
  *B01L 3/00* (2006.01)
  *B01L 99/00* (2010.01)
  *G01N 15/06* (2006.01)
  *G01N 33/00* (2006.01)
  *G01N 33/48* (2006.01)

(52) U.S. Cl.
  USPC ........................................ 422/500; 422/68.1

(58) Field of Classification Search
  USPC ......... 435/6.1, 6.11, 6.14, 91.2, 7.2, 29, 70.1, 435/174, 325, 283.1, 289.1; 422/50, 400, 422/417, 420, 68.1, 69, 500, 129, 600; 436/501, 8
  See application file for complete search history.

(56) References Cited

U.S. PATENT DOCUMENTS

| | | | | |
|---|---|---|---|---|
| 4,910,146 | A * | 3/1990 | Tur-Kaspa et al. | 435/420 |
| 5,002,377 | A * | 3/1991 | Battifora et al. | 359/398 |
| 6,103,518 | A | 8/2000 | Leighton | |
| 6,699,710 | B1 | 3/2004 | Kononen et al. | |
| 7,029,615 | B2 * | 4/2006 | Lilischkis et al. | 264/248 |
| 7,405,056 | B2 * | 7/2008 | Lam et al. | 435/40.5 |
| 2002/0009767 | A1 * | 1/2002 | Muraca | 435/40.5 |
| 2004/0197897 | A1 | 10/2004 | Leighton | |
| 2006/0216781 | A1 | 9/2006 | Gebing | |
| 2008/0318805 | A1 | 12/2008 | Fulton et al. | |

OTHER PUBLICATIONS

Koneonen (Jul. 1998) Nature Medicine vol. 4 pp. 84 to 847.*
Montgomery (Mar. 2005) Applied Immunohistochemistry and Molecular Morphology vol. 13 pp. 80 to 85.*
Kononen et al. (1998) Nature Medicine, vol. 4, No. 7, pp. 844-847.*
Battifora, Hector, "Methods in Laboratory Investigation—The Multitumor (Sausage) Tissue Block: Novel Method for Immunohistochemical Antibody Testing", *Laboratory Investigation, Division of Pathology, City of Hope National Medical Center*, Duarte, CA vol. 55, No. 2 Copyright by the United States-Canadian Division of the International Academy of Pathology 1986 , 244-248.
Battifora, Hector, et al., "Methods in Laboratory Investigation—The Checkerboard Tissue Block—An Improved Multitissue Control Block", *Laboratory Investigation, Division of Pathology, City of Hope National Medical Center*, Duarte, CA vol. 63, No. 5 Copyright by the United States and Canadian Academy of Pathology, Inc. 1990 , 722-724.
Eguiluz, Cesar, et al., "Multitissue Array Review: A Chronological Discription of Tissue Array Techniques, Applications and Procedures", *Pathology—Research and Practice, Elsevier GmbH*, vol. 202 available online at www.sciencedirect.com 2006 , 561-568.
Fedor, Helen L. et al., "Practical Methods for Tissue Microarray Construction", *Methods in Molecular Medicine*, vol. 103, *Pancreatic Cancer: Methods and Protocols* 2004 , 89-101.
Lebaron, Matthew J. et al., "Ultrahigh Density Microarrays of Solid Samples", *Lombardi Comprehensive Cancer Center, Department of Oncology, Georgetown University Medical Center, Nature Publishing Group, Nature Methods*, vol. 2 No. 7 Jul. 2005 , 511-513.
Moskaluk, Christopher A. et al., "Agarose Mold Embedding of Cultured Cells for Tissue Microarrays", *Diagnostic Molecular Pathology, Lippincott Williams & Wilkins, Inc.*, Philadelphia, PA, vol. 11, No. 4 2002 , 234-238.
Parsons, Mike et al., "How to Make Tissue Microarrays", *Diagnostic Histopathology, Elsevier Ltd.*, vol. 15, No. 3 2009 , 142-150.
Sarewitz, Stephen J, "Anatomic Pathology Checklist", *Commission on Laboratory Accreditation—Laboratory Accreditation Program, Anatomic Pathology* (Web File) Sep. 2007 , 45-46.
Theillet, Charles, "Full Speed ahead for Tumor Screening", *Nature Medicine*, vol. 4 No. 7 A new high-throughput tissue microarray technology is capable of simultaneously testing hundreds of tumor samples for a number of different molecular markers Jul. 1998 , 767-768.

* cited by examiner

*Primary Examiner* — Ardin Marschel
(74) *Attorney, Agent, or Firm* — Intellectual Innovations Legal Advisors

(57) ABSTRACT

A method and apparatus are provided for forming high-yield tissue microarray blocks capable of producing 1,000 or more replicate slides. In one embodiment, a plurality of donor tissue samples are minced and suspended in separate molten liquid carriers to form a plurality of separate two-phase mixtures of solid minced tissue and molten wax. Each of the two-phase mixtures is preferably formed into elongated columns and transferred into a separate well of a microarray block. A method and apparatus are provided for forming the elongated molten wax columns with minced tissue evenly distributed along the length of each column. The apparatus for forming the array includes an extrusion mechanism for transferring the columns of two-phase mixtures into the deep wells of the microarray block. The two-phase mixture may alternately be cooled and allowed to solidify before being transferred into the microarray block. An alternate embodiment is provided wherein cell cultures are utilized as starting material as opposed to solid donor tissue samples.

18 Claims, 10 Drawing Sheets

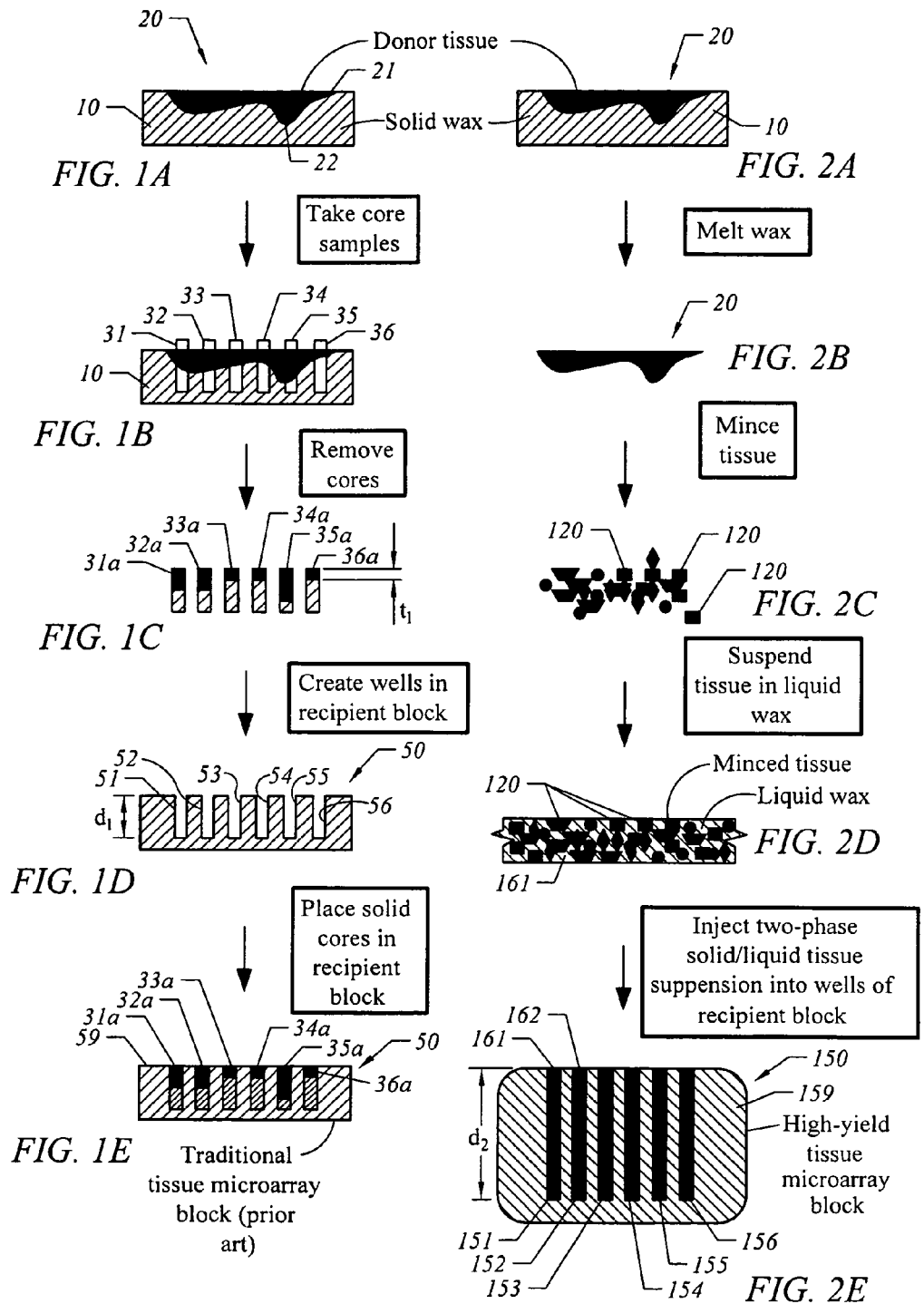

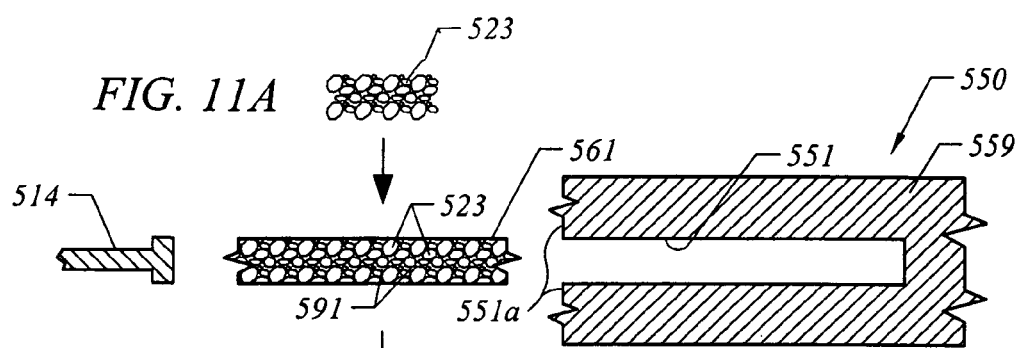
FIG. 11A
FIG. 11B
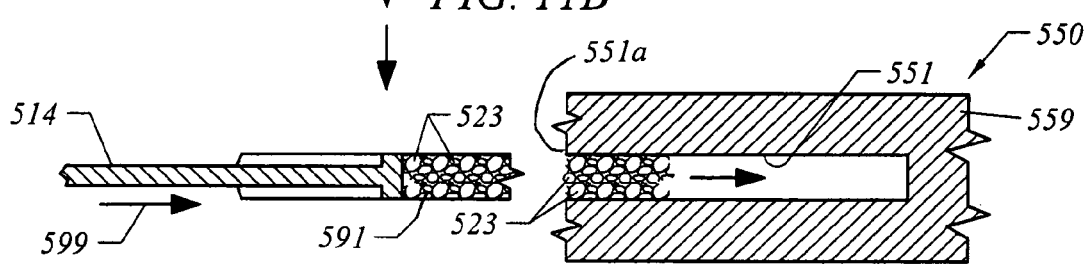
FIG. 11C
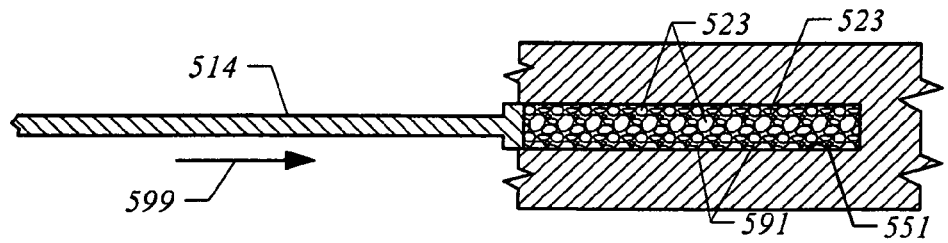
FIG. 11D
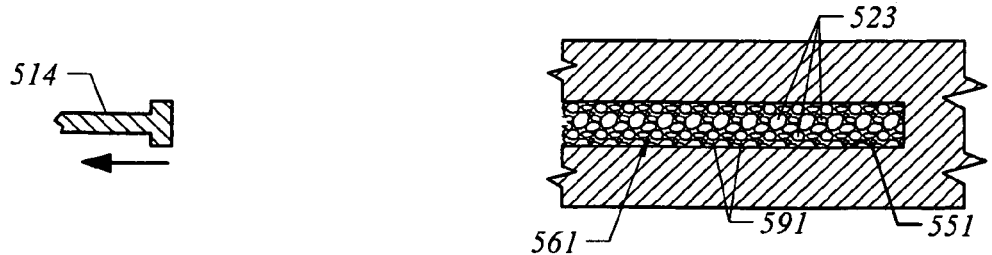
FIG. 11E

METHOD FOR PRODUCING TISSUE MICROARRAY BLOCKS

CROSS-REFERENCE TO RELATED APPLICATION

This application claims the benefit of and priority from U.S. provisional application Ser. No. 60/933,968 filed on Jun. 8, 2007.

BACKGROUND AND BRIEF SUMMARY OF INVENTION

The present invention relates generally to tissue arrays used in histology for medical and biological research as well as in medical diagnosis and treatment of disease.

The virtual explosion of knowledge in biotechnology in recent years has caused an enormous demand for tissue microarray blocks. These microarray blocks contain tissue samples that provide multiple on-slide tissues that are useful for a variety of purposes.

The prior art techniques for producing tissue microarray blocks typically involve transferring of solid core samples from a donor tissue sample into a blank recipient wax block. The thickness of these prior art solid core samples is determined by the thickness of the donor tissue. As an example, if the donor tissue has a thickness of 2 mm, the solid core sample transferred into a well of a prior art tissue microarray block will have that same 2 mm thickness. When sliced into sections for microscopy, that particular tissue sample can produce about 200 slides. In a prior art tissue microarray block having a plurality of wells containing different solid tissue samples with differing thicknesses, each well will produce a different number of "daughter" slides. This results in an inefficient technique, since the well with the thinnest solid core sample will determine the ultimate number of slides obtainable from the block. Therefore, in the prior art technique, the number of obtainable slides is limited, and there is also a waste of donor tissue.

There is clearly a dire need for a more efficient technique of producing tissue microarray blocks wherein each well of the block contains a solid tissue sample having a depth not determined by the thickness of the solid donor tissue. In fact, for the purposes of immunohistologic diagnosis, the College of American Pathologists has recommended multiple on-slide tissue controls for every patient (Commission On Laboratory Accreditation, Laboratory Accreditation Program Anatomic Pathology Checklist, S. Sarewitz, MD, Editor, September 2007, pp. 45-46). Given the enormous demand for tissue microarrays (TMAs) that this would represent, this goal has not yet been realized, and a more efficient method for TMA production is required. The present invention provides for more efficient TMA production and, in addition, achieves a "high-yield" tissue microarray block capable of producing many times more slides from a single block than the prior art!

The manner in which the present invention achieves these dramatic results is elegant in its simplicity. Rather than using solid, rod-shaped coring samples, one embodiment of the present invention "minces" the solid donor tissue into fragments. The fragments are embedded in a liquefied carrier having a low melting point, such as wax. The solid, minced fragments are evenly distributed throughout the length of the molten, liquefied carrier, forming a two-phase (i.e. solid and liquid) mixture. The two-phase mixture may be formed into the shape of a "deep well" and transferred into a microarray block while the carrier remains molten. In another embodiment, the two-phase mixture is cooled to solidify the carrier prior to being transferred into a "deep well," such as 17 mm long and 2 mm diameter, for example. By using this "mincing" technique together with forming the desired shape of a deep well, both objectives described above are achieved along with reduced waste of donor tissue. First, the thickness of the solid donor tissue transferred to each well is not limited to the thickness of the original donor tissue. Second, and equally important, the thickness of the tissue samples transferred into the wells of the block is uniform and of much greater thickness than the prior art. The result of the present invention is an efficient, cost effective, high quality and high yield tissue microarray block capable of producing 1,000 to 2,000 replicate slides, 5 to 10 times more than the prior art!

Alternatively, rather than "mincing" solid donor tissue, homogenous tissue derived from cell culture may be used and, after appropriate fixation, suspended in a liquid carrier and transferred in liquid form into a deep well. In a distinct version of the technique, the mixture of cell culture material and carrier can be allowed to solidify within a duct of cross-sectional size and shape approximately equal to that of the deep well, and subsequently transferred in solid form into the deep well by simple extrusion from said duct, via the simple application of force by a plunger or other means. Both of these techniques differ from prior art techniques using cell cultures to form TMAs, in that the prior art solidifies the mixture of cell culture and carrier (by centrifugation, re-suspension in a carrier and solidification of the mixture) and then takes core samples of the resulting solid material (Moskaluk and Stoler, "Agarose Mold Embedding of Cultured Cells for Tissue Microarrays," *Diagnostic Molecular Pathology* 11(4): 234-238, 2002; also Montgomery et al, "A Novel Method for Making 'Tissue' Microarrays From Small Numbers of Suspension Cells," *Applied Immunohistochemistry & Molecular Morphology*, 13(1): 80-84, 2005).

Another aspect of the present invention is a novel system for forming the two-phase mixture of minced solid donor tissue into elongated columns (17 mm long and 2 mm in diameter, for example) of a meltable carrier such as wax. An elongated passageway is formed in a body of thermally conductive, preferably transparent material. A source of sufficient heat is applied to the passageway in order to maintain part or all the length of the passageway above the melting-point temperature of the carrier substance. Paraffin wax is a good example of a suitable carrier, but other substances can also be used. Molten carrier is transferred into the elongated passageway by one or more of several means: (a) the pure carrier substance may be introduced in the molten state from a heated dispenser; (b) the pure carrier substance may be introduced in the solid state, relying on the temperature of the passageway to melt the carrier; (c) tissue samples may be embedded in the carrier substance, which melts due to the temperature of the passageway. Option (c) is often preferable in the case of minced solid tissue fragments. In any case, the minced solid donor tissue fragments, or other tissue constituents, such as obtained from cell cultures, are introduced to the passageway along with the molten carrier substance, thus creating a two-phase mixture (suspension of biological material in liquid carrier). At the entrance of the passageway may exist a collecting receptacle or "hopper," also heated, to facilitate the melting of carrier and the mixing of biological material in liquid carrier. A duct originates in the hopper and intersects the passageway. With or without the use of a hopper, the liquid carrier and biological material are inserted into the passageway. Some means of propelling this two-phase mixture through the passageway is implemented, such as: (a) pressing with a plunger that contacts the mixture and propels it similarly to the action of a syringe; (b) the application of hydraulic pressure to the passageway after sealing any sideports such as the intersecting duct from a hopper; (c) gravity-driven flow of the mixture; (d) propulsion of the mixture by direct contact with an auger feeder within the passageway. It is the liquid state of the carrier during this step that enables such a range of possible propulsion mechanisms, and also in general enables the mixture to flow through a duct with curvature, converging and/or diverging sections. During its travel through the passageway, the velocity and temperature of the mixture are controlled by the speed or pressure of the propulsion mechanism and, if necessary, the management of heat applied to the passageway, order to form the mixture into a dense column and to control the state of liquidity of the carrier substance. Some degree of cooling, in order to increase the viscosity of the liquid carrier, or even to solidify it, can be advantageous near the end of the passageway. The compressed tissue column is then extruded out of the elongated passageway into a well within a recipient block.

In the case where the biological material for the microarray comes from a solid human or animal tissue source, the mincing step must be done in order to obtain a sufficiently pure tissue of interest, and with techniques appropriate to the type of tissue and to the required orientation of tissue structures in the product slides and hence in the microarray block. In summary, the process of mincing depends on the type of tissue. In many cases, skilled dissection by hand is required, but in other cases mincing can be done by an automated fragmenting process such as with sharp rotating blades. As used herein and in the claims, the term "mincing" is used in a broad sense to include (a) simple fragmentation of a solid tissue sample that has been previously selected for its purity of tissue type, when purity of tissue type is sufficient for the purposes of the resulting microarray analysis; (b) careful dissection into fragments of a more precisely specified biological and physical structure, when such precision is necessary in order that the required biological and physical structures are present in the resulting microarray. Two illustrative examples are provided in the next paragraph.

Careful dissection may be required to harvest the tissue of interest at various steps depending on the tissue chosen. Illustration is provided by way of two examples that demonstrate some of the range of precision required for different tissue types. Colonic epithelium is harvested from a colonic resection specimen, preferably one that is non-fixed. The colon is opened longitudinally, using sharp dissection (scalpel blade) to separate the mucosa from the underlying fibromuscular soft tissue. Sheets of colonic mucosa are obtained in this manner and are cut into small sections of appropriate size for placing in plastic histology cassettes (up to about 20 mm×10 mm×4 mm). The sectioned mucosa is submitted in cassettes for routine histologic fixation and "processing" (dehydration and embedding in wax). After processing, the wax shroud is melted away, and the solid tissue is minced with a scalpel blade. Minced fragments should be on the order of 2 mm×2 mm×2 mm. The size of the fragments and their orientation can be important in some circumstances. For instance, skin fragments should have a long axis parallel to the plane of the dermal-epidermal junction, and this axis should be loaded parallel to the long axis of the "barrel" of the injector, such that the dermal-epidermal junction is ultimately visualized in cross-section on the microscope slide.

A further aspect of the present invention is a novel apparatus for forming the recipient (blank, open-well) microarray blocks. The apparatus provides an efficient system for forming the required array of much deeper wells than the wells of the prior art. The apparatus includes a means of easily varying the number and configuration of wells by removable/configurable pins in a mold device. This is useful for customizing the size and shape of the array. However, it should be noted that a casting technique is not the only way to produce the recipient microarray blocks. For example, an alternative and efficient method would be to use a drilling, reaming, and/or milling method for creating deep wells in an initially solid block of machinable wax, using a manual or computer numeric controlled (CNC) milling or drilling machine.

The prior art techniques of forming tissue arrays are summarized in the article by Eguiluz et al entitled "Multitissue array review: A chronological description of tissue array techniques, applications and procedures" published in Pathology-Research and Practice 202 (2006) at pp. 561-568 and in U.S. Pat. Nos. 6,103,518 and 7,029,615.

As noted above, the first embodiment of the present invention differs significantly from the prior art by using minced solid tissue fragments to form a two-phase mixture with a molten carrier such as wax. The prior art uses core samples of solid donor tissue. The mincing (and suspension) technique inherently allows the use of more uniform length wells and deeper wells than the prior art with less waste of donor tissue.

A primary object of the invention is to provide a high yield tissue microarray block wherein minced solid donor tissue fragments are suspended in a meltable or molten carrier such as wax.

An object of a second embodiment of the invention is to construct microarrays where the source of biological material comes from another source such as cell culture.

A further object of the invention is to provide a tissue microarray block wherein each well has an increased depth not determined or limited by the thickness of the donor tissue.

Another object of the invention is to provide a method and apparatus for forming elongated columns of a meltable carrier, such as wax, wherein suspended fragments of minced solid donor tissue are distributed evenly over the length of the column.

Another object is to provide an apparatus for forming a tissue microarray block having a plurality of wells wherein each well has a depth significantly greater than prior art wells.

Other objects and advantages will become apparent from the following description and drawings.

BRIEF DESCRIPTION OF THE DRAWINGS

FIGS. 1A-1E are schematic illustrations of a typical prior art method of preparing a tissue microarray block;

FIGS. 2A-2E are schematic illustrations of a method of forming a high yield microarray block according to the present invention;

FIG. 11 is a schematic representation of an alternate embodiment of the invention utilizing a cell culture rather than a solid donor tissue.

DETAILED DESCRIPTION OF DRAWINGS

Figure 3:
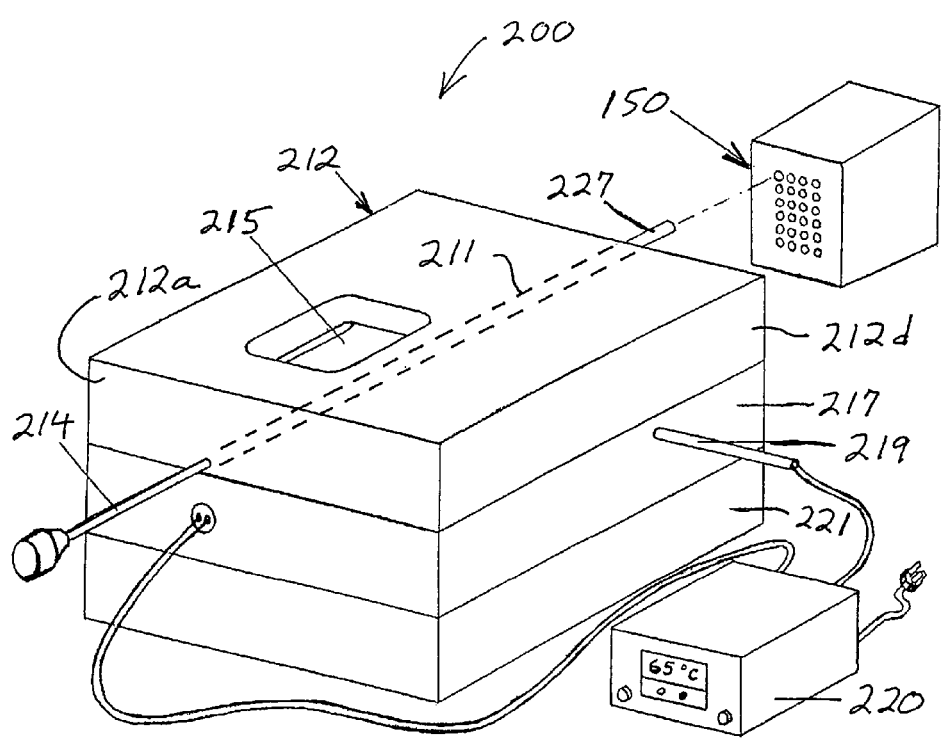
FIG. 3 is a perspective view of an apparatus for forming the individual two-phase columns of solid minced tissue and molten carrier according to the present invention.

FIGS. 1A-1E and 2A-2E are concept sketches which compare and contrast the methodologies of the prior art (FIGS. 1A-1E) and the present invention (FIGS. 2A-2E).

As shown in FIG. 1A, a sample of solid donor tissue 20 is shown as being stored or embedded in a body of solid wax 10, usually formalin fixed. The donor tissue is typically irregular in shape, typically having a region 21 of minimum thickness and a region 22 of maximum thickness.

As shown in FIG. 1B, and according to typical prior art methodology, a plurality of coring tubes 31-36 are forced downwardly through donor tissue sample 20 in order to transfer portions of the donor sample into the coring tubes or punches.

As shown in FIG. 1C, the coring tubes 31-36 are then removed from the sample donor tissue; FIG. C shows only the core tissue samples 31a-36a and does not show coring tubes 31-36. Each core tissue samples 31a-36a contains a different thickness of donor tissue. For example, core tissue sample 36a contains a donor tissue sample 36a having a thickness $t_1$.

As shown in FIG. 1D, a prior art recipient block 50 is typically formed of wax, having wells 51-55 with a depth of $d_1$. A common prior art depth is 2 mm to 4 mm.

As shown in FIG. 1E, the next step in the typical prior art system is to transfer the cylindrical tissue core samples 31a-36a into the wells 51-56 of recipient block 50, usually made of paraffin wax.

As is known in the prior art, the upper surface 59 of block 50 is sliced to obtain "daughter slices" of each of the core tissue samples 31a-36a. Since core sample 36a has the smallest thickness $t_1$ of each of the samples 31a-36a, it will determine or limit the number of tissue samples that may be obtained from all of the wells 51-56 of recipient block 50.

FIGS. 2A-2E illustrate conceptually the methodology of the present invention.

As shown in FIG. 2A, the same sample solid donor tissue 20, as shown in FIG. 1A, is stored in a body of solid wax 10 as is known in the art.

As shown in FIG. 2B, according to the present invention, the wax body 10 has been melted and the tissue sample 20 has been separated from the wax body 10.

As shown in FIG. 2C, the solid tissue sample 20 has been "minced" into hundreds or thousands of solid tissue fragments 120. The mincing can be done by a variety of techniques known in the art, preferably by repeated slicing with sharp blades to produce relatively uniform sized fragments 120.

As shown in FIG. 2D, the minced fragments 120 are then transferred into preferably elongated, horizontal columns of molten wax such as column 161. As described below, vertical columns may also be utilized. The fragments 120 are introduced into the elongated wax column 161 in a fashion (described in greater detail below), preferably to ensure that the fragments 120 are distributed evenly throughout the length of elongated column 161.

As shown in FIG. 2E, according to the present invention, a high yield tissue microarray block 150 is provided having a body 159 and a plurality of relatively deep wells 151-156. Each of the wells 151-156 is preferably cylindrical and preferably approximately 15 mm in depth and having a cross sectional diameter of approximately 2 mm. These dimensions are by way of example. It is to be understood that the well dimensions may be varied from the example given.

The depth $d_2$ of each of the wells 151-156 is preferably 15 mm to 20 mm or approximately 5 to 10 times greater than the depth $d_1$ of prior art tissue microarray blocks. Since the tissue fragments 120 are continuously distributed over the length of elongated column 161 carried in well 151, usable "daughter slides" (or tissue microarray sections) can be obtained throughout the entire depth $d_2$ of each of the elongated columns, such as 161 and 162, carried in wells 151-156 of the present invention. It is also significant to note that the present invention uses essentially all of the sample donor tissue 20 and avoids waste of the sample tissue that is inherent in the prior art core sample technique described above.

FIGS. 3-6 illustrate the preferred method and apparatus of the present invention for preparing a liquid suspension of minced tissue fragments in molten wax and then extruding the suspension into the blank wells of the novel tissue microarray block of the present invention. The extrusion device is shown generally as 200 and includes a housing 212 having an elongated passageway 211 which extends through housing 212 from the front wall 212a and through the rear wall 212b. An elongated plunger 214 is mounted such that it can slide in the elongated passageway 211. A hopper 215 is formed in the top surface 212c of housing 212 and extends downwardly and communicates with elongated passageway 211. Housing 212 preferably has three layers, including a top, thermally conductive layer 212d, a middle metallic layer 217, and a lower polycarbonate, insulating layer 221. Housing 212 is preferably positioned adjacent microarray block 150. An exit nozzle 227 is a thin walled tube that is carried in passageway 211 and forms an extension of elongated passageway 211. Nozzle 227 reduces or prevents leakage of the two-phase mixture as the mixture is transferred into the wells 151-152 as shown best in FIG. 6C.

Figure 6A:
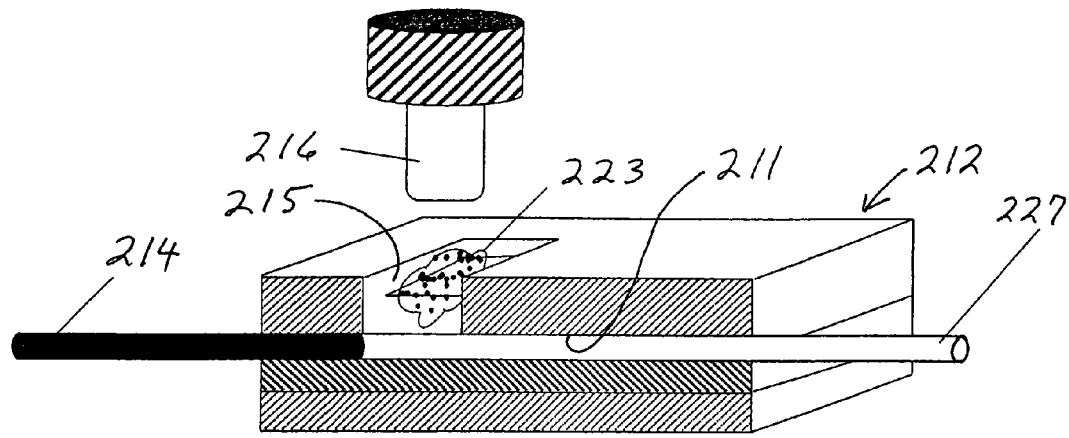
FIG. 6A is a schematic showing the preliminary loading of the two-phase minced tissue and wax mixture into a hopper.
Figure 6B:
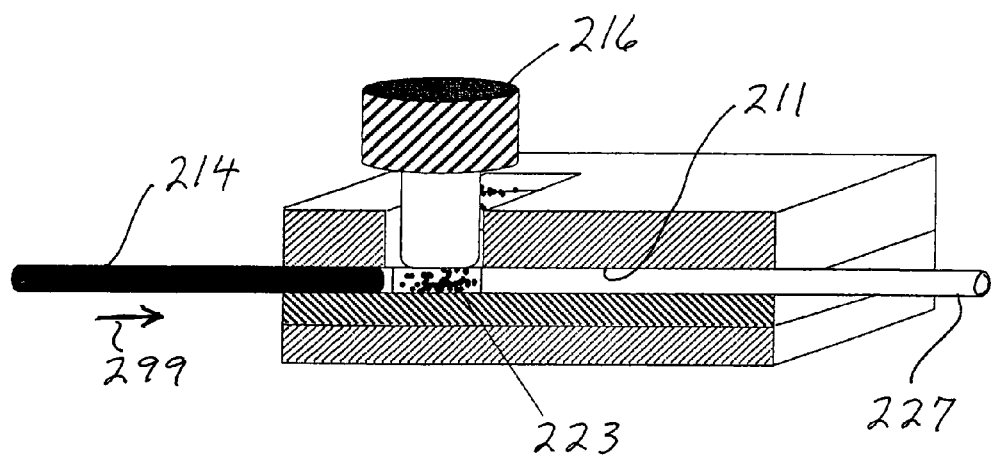
FIG. 6B is a schematic illustrating how the tamper shown in FIG. 6A is loading the solid minced tissue and wax mixture into the elongated passageway shown.
Figure 6C:
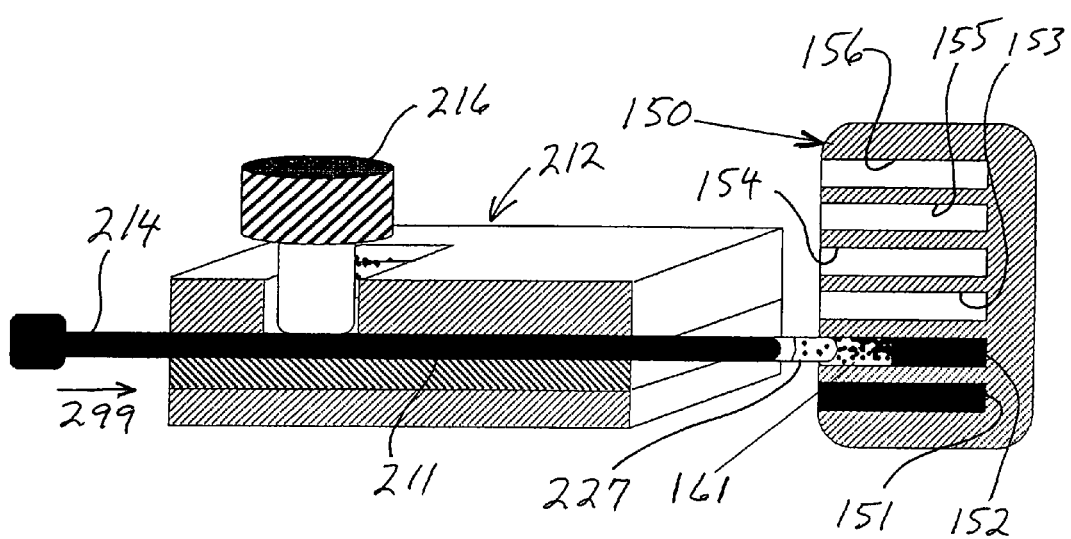
FIG. 6C is a schematic illustrating how the solid minced tissue and wax mixture is transferred or extruded into a deep well of a tissue microarray block according to the present invention.

Referring to FIGS. 6A-6C, minced tissue fragments 223 which have been previously trimmed (and preferably formalin-fixed and embedded in paraffin) are added to the hopper 215. A heating element 218 (FIG. 4) in thermal contact with passageway 211 causes the wax (in the solid state) in which the tissue fragments are embedded to melt, creating a liquid suspension of tissue. Additional solid or liquid wax (or other low melting point carrier) can be added to the hopper 215 as needed to provide a sufficient amount of liquid carrier for management of flow and elimination of bubbles and/or voids. It is also possible to process tissue fragments such as 223 that are not initially embedded with wax or other low melting point carrier material; the desired liquid for the suspension can be created fully by adding solid or liquid carrier to the hopper 215.

The two-phase (i.e. liquid carrier and solid tissue fragments) mixture is then pressed downwardly into the elongated passageway 211 with a tamper 216. The tamper 216 is then used to seal the passageway, while the plunger 214 is utilized to compact the tissue fragments and melted carrier into a continuous column 161 (FIG. 6C) by advancing the plunger 214 from its position shown in FIG. 6B in the direction of arrow 299.

As shown best in FIG. 6C, the high yield tissue microarray block 150 as shown in FIG. 2E is positioned adjacent housing 212 with the wells 151-156 oriented in a horizontal fashion and aligned in a fashion so at least one of the wells 151-156 is aligned with elongated passageway 211. As shown in FIG. 6C, plunger 214 is extruding the two-phase mixture of solid minced tissue and liquid carrier through thin walled tube or nozzle 227 into deep well 152 as a two-phase column of predetermined length shown as 162 in FIG. 2E in its finished form. Also shown in FIG. 6C is well 151 having previously been filled with a similar column 161 comprising a two-phase mixture of tissue fragments and molten wax wherein the column 161 has a uniform distribution of solid minced tissue over its length.

Alternatively, the column 161 of predetermined length may be allowed to cool and solidify in passageway 211 prior to being transferred or extruded into a well of a microarray block.

The outer diameter of the elongated passageway 211 is approximately the same size as the inner diameter of each of the wells 151-156 of tissue microarray block 150. The process is repeated to fill all of the wells 151-156 in block 150. The block 150 is then "cured" by uniformly heating the entire tissue microarray block in an oven, for example, to a softening temperature (typically, 45° Celsius for 30 minutes) to promote bonding between the tissue/wax mixture in each well and the surrounding wax block 150. It should be noted that this curing step may be similarly advantageous to be applied in conjunction with any of the methods stated herein for producing tissue microarray blocks, as a final step after transfer of tissue/wax mixture into the wells of the recipient block.

Figure 4:
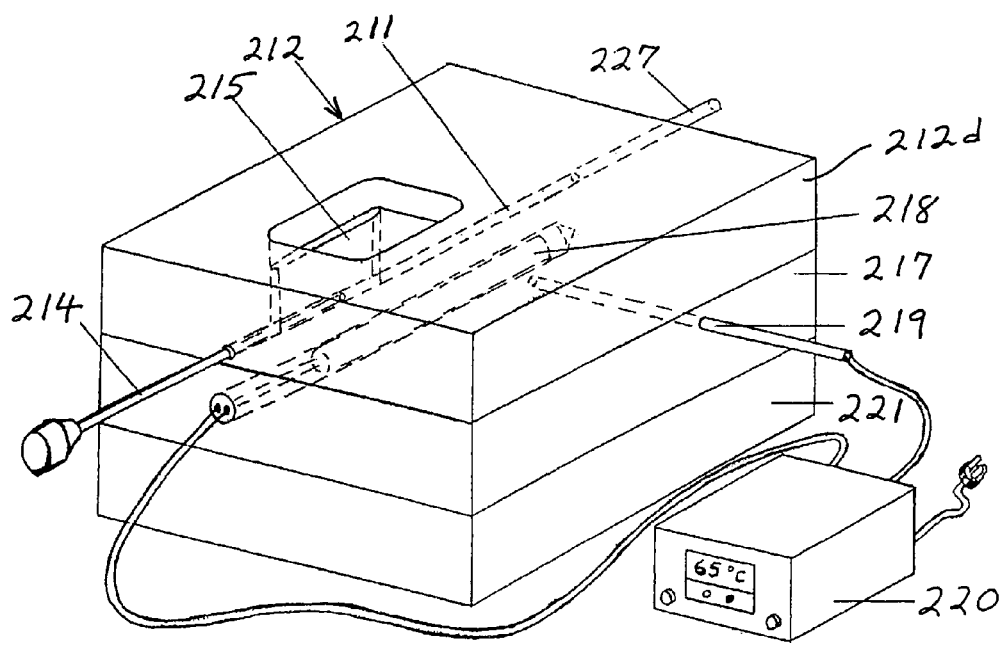
FIG. 4 is a perspective view of the apparatus shown in FIG. 3 which also includes the heating device and temperature sensor according to the present invention.
Figure 5:
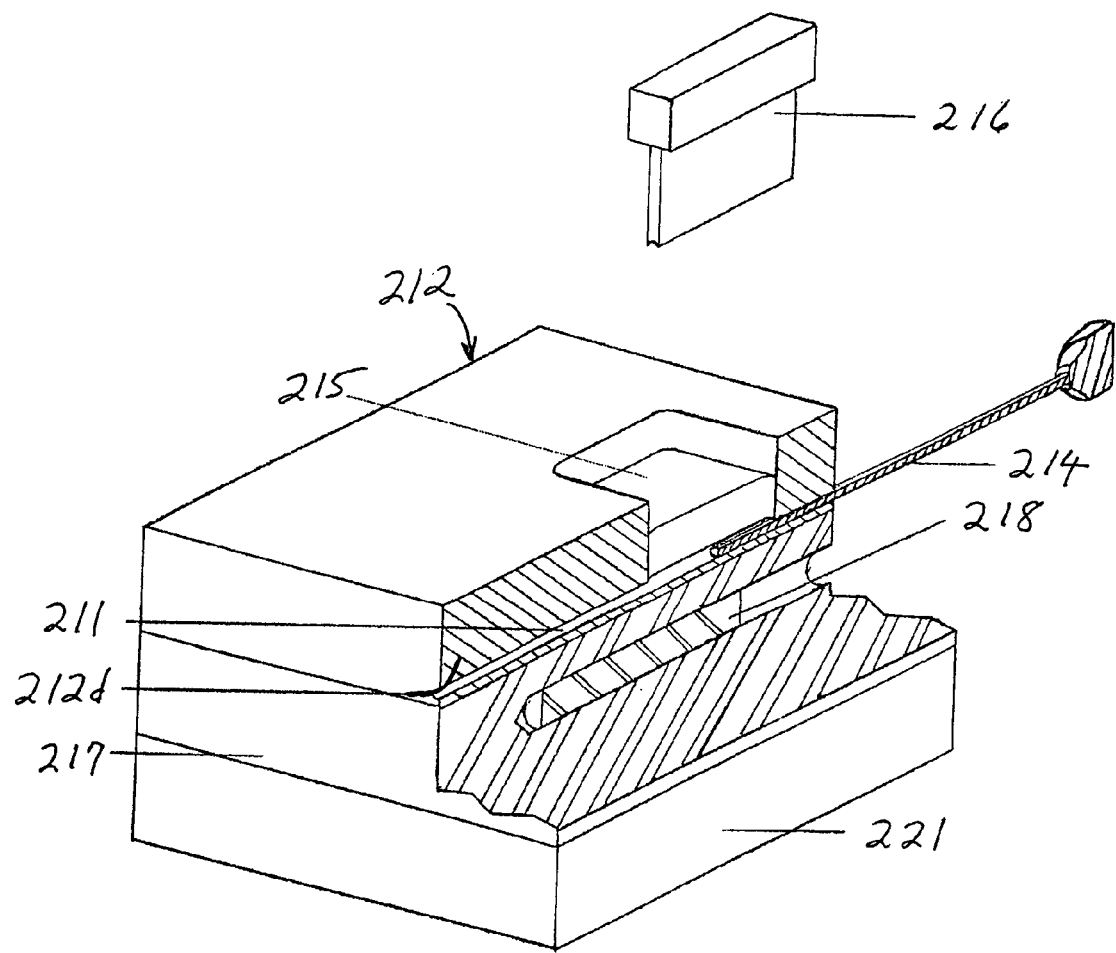
FIG. 5 is a reverse perspective view of the apparatus shown in FIGS. 3 and 4, partially in section and which also includes a tamper according to the present invention.

As shown best in FIG. 4, a heater 218 capable of heating housing 212 to approximately 65-80° Celsius is embedded in housing 212 and is in thermal contact with elongated passageway 211. A temperature sensor 219 is also embedded in housing 212 and monitors operating temperatures of the device. A controller 220 is provided which may be either a voltage controller or feedback process controller utilizing the temperature sensor 219 as an input to control the output of heater 218 in order to control the temperature of material within elongated passageway 211.

Figure 7:
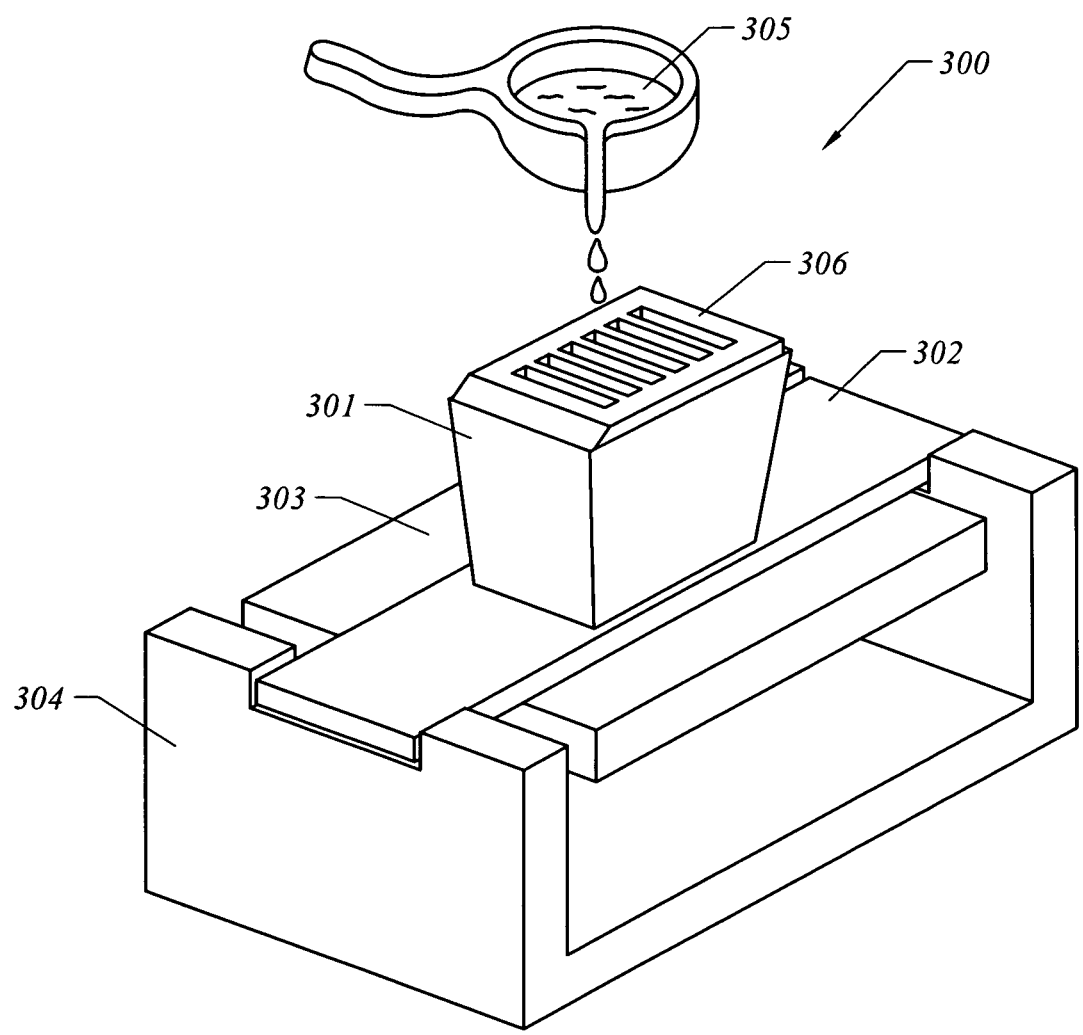
FIG. 7 is a perspective view of a casting apparatus used in conjunction with the present invention.
Figure 8:
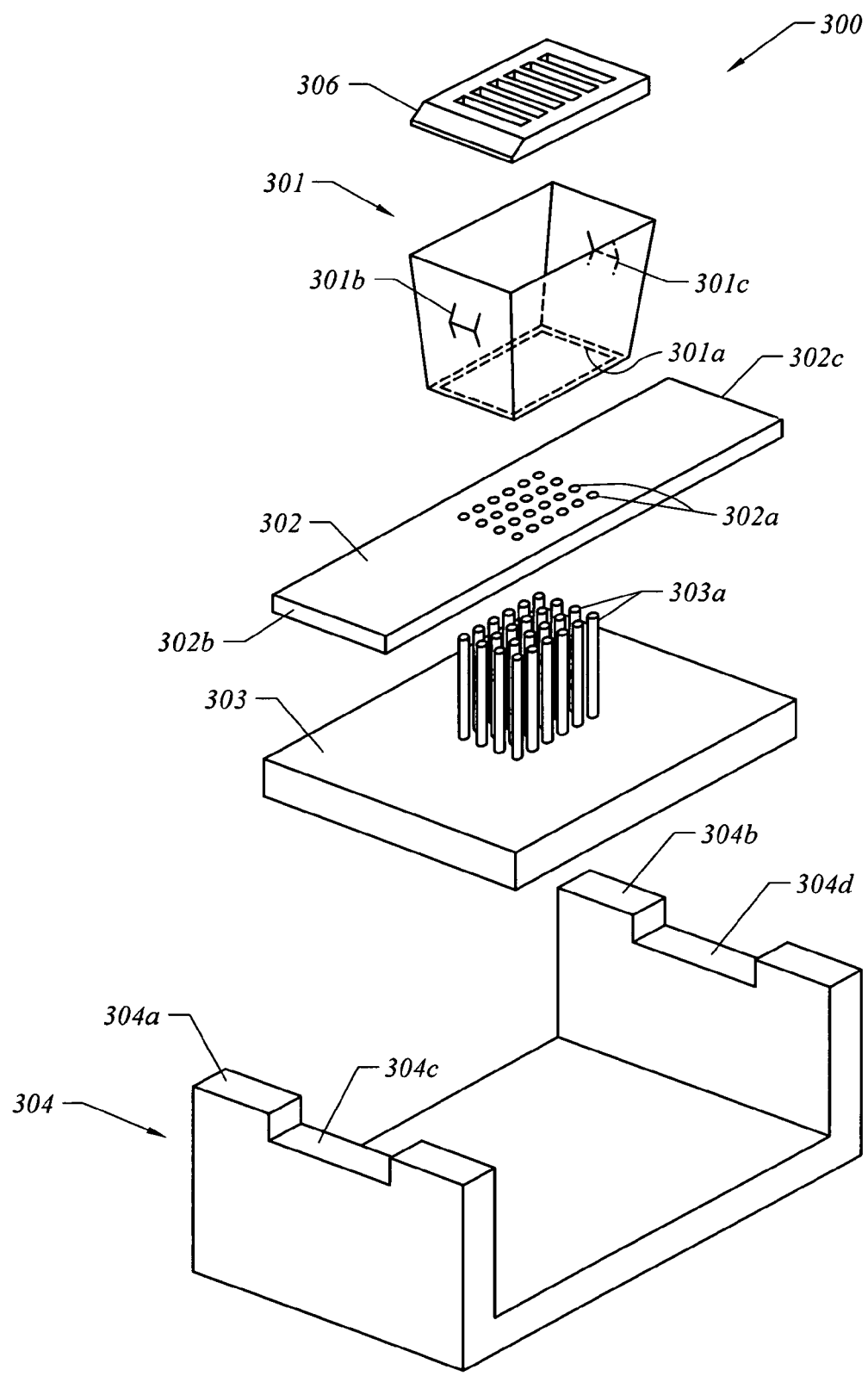
FIG. 8 is an exploded view of the apparatus of FIG. 7.

FIGS. 7 and 8 illustrate the apparatus preferably utilized for forming the paraffin blocks (such as 150 in FIG. 2E) with preformed deep wells in a grid pattern array for use in conjunction with the present invention. The casting apparatus is shown generally as 300 in FIG. 7 and is shown in an exploded view in FIG. 8. As shown in FIG. 8, a modified deep histology block mold 301 is illustrated. The floor 301a has been modified to create an opening to receive the pin assembly 303 described below. Mold 301 includes upwardly oriented wings 301b and 301c on the short sides to enable release of the wax block (not shown in FIG. 8 for clarity), by inverting the mold 301 and tapping the wings 301b and 301c on a hard surface.

An ejector plate 302 is provided which is an elongated rectangular plate with an array of holes 302a formed therein. The purpose of ejector plate 302 is to separate the cast block (not shown) and mold 301 from the pin array assembly 303. Each pin of the pin array assembly 303a preferably has a length of between 15 mm and 20 mm and a diameter of preferably 2 mm to 3 mm (as noted above). It is understood that the pins could be larger or smaller and they could have a non-circular shape. The pins form the deep wells of the finished block as shown as wells 151-156 in FIG. 2E above.

A bridge assembly 304 is provided and cooperates with the ejector plate 302 to facilitate the separation of the formed wax block (not shown in FIG. 8) from the pin assembly 303a. The bridge assembly 304 includes first and second upstanding end pieces 304a and 304b. The end pieces 304a and 304b are recessed as shown at 304c and 304d to receive the ends 302b and 302c of ejector plate 302.

It is to be understood that various techniques may be utilized to form the above-described two-phase mixture of minced tissue fragments and molten wax into an elongated, preferably cylindrical column.

Molten wax 305 (FIG. 7) is poured through a slotted cover 306 into mold 301 (FIG. 7).

Figure 9:
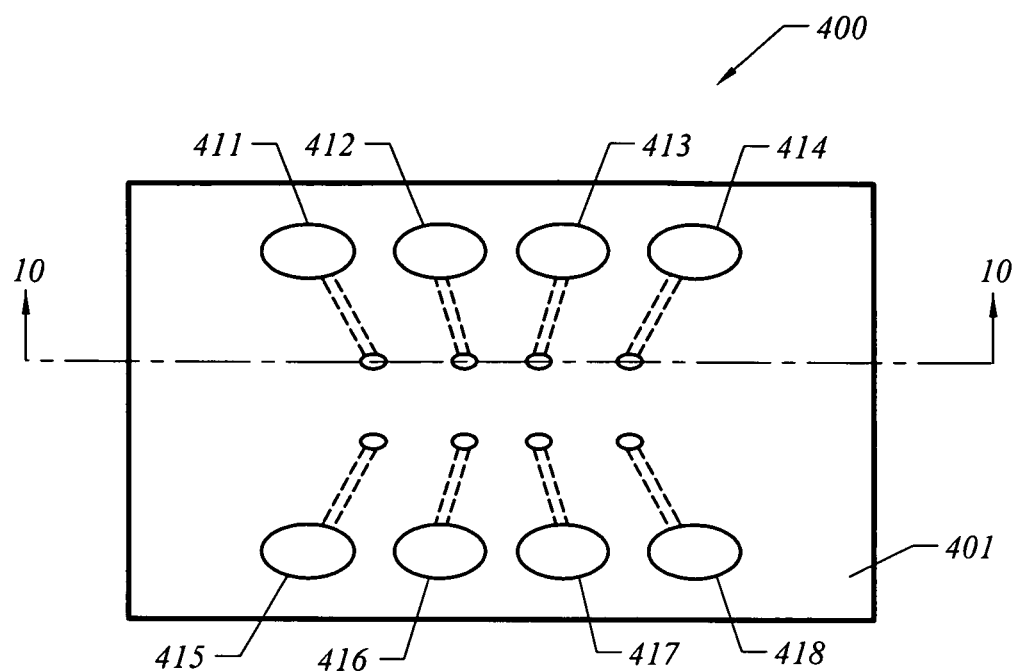
FIGS. 9 and 10 show an alternate apparatus according to the present invention utilized to simultaneously prepare and transfer multiple mixtures of minced fragments and molten wax into a plurality of wells of a tissue microarray block according to the present invention.
Figure 10:
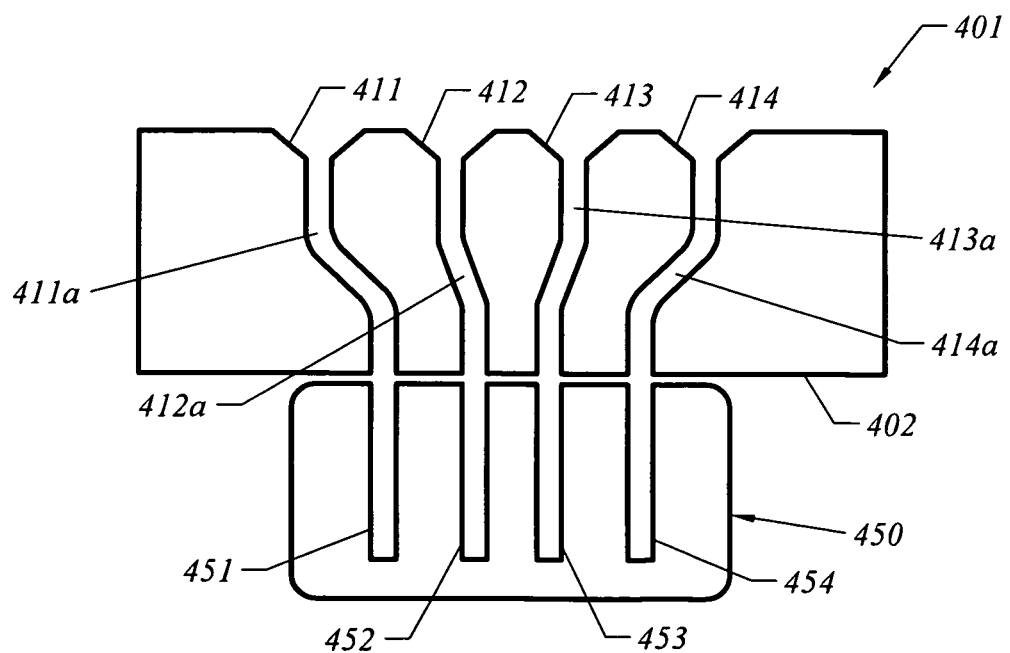

FIGS. 9 and 10 illustrate an alternate embodiment of the apparatus and method shown in FIGS. 3-6. Whereas the embodiment shown in FIGS. 3-6 and described above produces single, two-phase horizontal columns, the embodiment shown in FIGS. 9 and 10 may be utilized to produce multiple two-phase mixtures of tissue fragments and molten wax simultaneously.

As shown in FIG. 9, a device shown generally as 400 includes a housing 401 in which a plurality of generally circular hoppers 411-418 is formed. Each of the hoppers 411-418 is adapted to receive minced tissue fragments along with wax either in liquid or solid form. As shown in FIG. 10, each of the hoppers 411-414 has a downwardly extending elongated passageway 41 1a-414a extending downwardly through the bottom surface 402 of body 401 forming a manifold.

As shown in FIG. 10, a deep well block 450 (made of wax) according to the present invention having vertical or slightly inclined wells 451-454 is positioned adjacent to and immediately below the lower surface 402 of housing 401. The deep wells 451-454 are also aligned with the lower ends of elongated passageways 411a-414a. In this fashion, multiple two-phased samples can be formed and transferred simultaneously into a plurality of wells of the novel deep well tissue block of the present invention. As shown in FIGS. 9 and 10, eight wells may be filled simultaneously, only four of which (411-414) are visible in FIG. 10. Each well 411-414 has a continuous distribution of minced tissue (or cultured cells) from the bottom to the top of each well.

FIGS. 9 and 10 are schematic illustrations which do not include heating elements and temperature sensing elements such as shown and described above for the sake of brevity.

FIGS. 11A-11E are "concept" sketches illustrating the alternate embodiment of the invention wherein a homogenous tissue sample 523 is derived from a cell culture and is used as a "starting material" rather than a solid donor tissue sample 20 as shown in FIGS. 1A and 2A and described above. As shown in FIG. 11B, the tissue sample 523 has been scraped or otherwise removed from the container in which it has been cultured (e.g. plastic flask or petri dish) or in which it has been densified by centrifugation (e.g. centrifuge tube) and dispersed into a preferably horizontally disposed column 561 of molten carrier 591 such as wax. Column 561 is held in a cylindrical duct or chamber (not shown in FIG. 11 for clarity), such as 211 in FIG. 6A. As used herein and in the claims, the word "cylindrical" is defined in a broad sense to include elongated shapes with circular, oval, elliptical, rectangular and triangular cross-sections. The elongated column 561 is formed adjacent a deep well block 550 having a body 559 and a plurality of deep wells, such as deep well 551. As shown in FIG. 11C, a piston or extrusion rod 514 is actuated and is caused to move in the direction of arrow 599 to transfer the elongated column 561 with dispersed cells of sample 523 in molten wax 591 directly into the deep well 551 of block 550. Appropriate measures are taken to prevent spillage or leakage of the molten column 561 as the transfer illustrated in FIG. 11C is taking place. For example, deep well 551 may have an extension (not shown) formed around its outer lip 551a to prevent leakage. Furthermore, the molten column 561 may be somewhat cooled prior to transfer to form a viscous two-phase mixture (or a single phase solid) in order to reduce spillage or leakage. As shown in FIG. 11D, the plunger or extrusion piston 514 has been driven in the direction of arrow 599 toward deep well 551 and has completely filled deep well 551 with the dispersed cells of sample 523 carried in molten wax 591. As shown in FIG. 11E, molten wax 591 has been allowed to cool and solidify in well 551 prior to the withdrawal of the plunger 514. As shown in FIG. 11E, deep well 551 has been filled with a continuous distribution of cells from sample 523 throughout the length of deep well 551.

The foregoing description of the invention has been presented for purposes of illustration and description and is not intended to be exhaustive or to limit the invention to the precise form disclosed. Modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A method for use with a plurality of animal or human donor tissue samples and a paraffin recipient block provided with a plurality of wells each having a cross-sectional size and shape to form a high yield tissue microarray block, comprising the steps of:
   cutting each one of said plurality of animal or human donor tissue samples into a plurality of tissue sample fragments,
   suspending each plurality of tissue sample fragments in a separate liquid carrier to form a two phase mixture of solid tissue sample fragments and liquid carrier for each plurality of tissue sample fragments,
   compacting each of said two phase mixtures of solid tissue sample fragments and liquid carrier into a chamber to take the form of a column for use in a high yield tissue microarray block, and
   transferring each of said columns from the chamber into at least one of said plurality of wells of said paraffin recipient block to create the high yield tissue microarray block, the chamber having a cross-sectional size and shape approximating the cross-sectional size and shape of the at least one of said plurality of wells,
   the length of each of said columns being independent of the size of the respective donor tissue sample.

2. The method of claim 1 wherein said transferring step includes transferring the carrier in each of said columns in a liquid state into the recipient block.

3. The method of claim 1 further comprising cooling the carrier in each of said columns prior to the transferring step so as to transform the carrier from a liquid state to a solid state.

4. The method of claim 1 wherein each said separate liquid carrier is a molten wax.

5. The method of claim 4 wherein said chamber is an elongated passageway and wherein said compacting step includes causing each of said two phase mixtures of solid tissue sample fragments and molten wax to separately pass into the elongated passageway to form a separate column.

6. The method of claim 4 wherein each of said plurality of donor tissue samples is disposed in a separate wax and wherein said suspending step includes heating each separate wax to form said respective molten wax.

7. The method of claim 1 wherein said compacting step includes pressing each of said two phase mixtures of solid tissue sample fragments and molten wax into said chamber.

8. The method of claim 5 wherein said compacting step includes cooling each of said two phase mixtures of solid tissue sample fragments and molten wax in said elongated passageway.

9. The method of claim 5 wherein said suspending step includes embedding each plurality of tissue sample fragments in a separate wax.

10. The method of claim 1 where said transferring step includes extruding each of said columns from a passageway.

11. The method of claim 1 wherein said compacting step includes utilizing a plunger to compact each of said two phase mixtures in the chamber.

12. The method of claim 1 wherein said transferring step includes causing each of said columns to flow into at least one of said plurality of wells.

13. A method for use with an animal or human donor tissue sample and a paraffin recipient block provided with a plurality of wells each having a cross-sectional size and shape to form a high yield tissue microarray block, comprising the steps of:
    cutting the animal or human donor tissue sample into a plurality of tissue sample fragments,
    suspending the plurality of tissue sample fragments in a liquid carrier to form a two phase mixture of solid tissue sample fragments and liquid carrier,
    compacting the two phase mixture of solid tissue sample fragments and liquid carrier into a chamber to take the form of a column for use in a high yield tissue microarray block, and
    transferring the column from the chamber into at least one of the plurality of wells of the paraffin recipient block to create the high yield tissue microarray block, the chamber having a cross-sectional size and shape approximating the cross-sectional size and shape of the at least one of the plurality of wells.

14. The method of claim 13 wherein the transferring step includes transferring the carrier in the chamber in a liquid state into the recipient block.

15. The method of claim 13 further comprising cooling the carrier in the chamber prior to the transferring step so as to transform the carrier from a liquid state to a solid state.

16. A method for use with an animal or human donor tissue sample and paraffin recipient block having a plurality of wells each having a cross-sectional size and shape to form a high yield tissue microarray block, comprising the steps of:
    cutting the animal or human donor tissue sample into a plurality of tissue sample fragments,
    suspending the plurality of tissue sample fragments in a liquid carrier to form a two phase mixture of solid tissue sample fragments and liquid carrier,
    compacting the two phase mixture of solid tissue sample fragments and liquid carrier into a chamber to take the form of an elongate segment for use in a high yield tissue microarray block, and
    transferring the elongate segment from the chamber into at least one of the plurality of wells of the paraffin recipient block to create the high yield tissue microarray block, the chamber having a cross-sectional size and shape approximating the cross-sectional size and shape of the at least one of the plurality of wells.

17. The method of claim 16 wherein the transferring step includes transferring the carrier in the elongate segment in a liquid state into the recipient block.

18. The method of claim 16 further comprising cooling the carrier in the elongate segment prior to the transferring step so as to transform the carrier from a liquid state to a solid state.

* * * * *